United States Patent
Rangan

(10) Patent No.: US 11,529,095 B2
(45) Date of Patent: ***Dec. 20, 2022

(54) RESEARCH PERFORMANCE FRAMEWORK

(71) Applicant: Federal Express Corporation, Memphis, TN (US)

(72) Inventor: Suresh Rangan, Frisco, TX (US)

(73) Assignee: Federal Express Corporation, Memphis, TN (US)

( * ) Notice: Subject to any disclaimer, the term of this patent is extended or adjusted under 35 U.S.C. 154(b) by 226 days.

This patent is subject to a terminal disclaimer.

(21) Appl. No.: 16/928,561

(22) Filed: Jul. 14, 2020

(65) Prior Publication Data

US 2020/0337632 A1  Oct. 29, 2020

Related U.S. Application Data

(63) Continuation of application No. 14/460,995, filed on Aug. 15, 2014, now Pat. No. 10,799,175.

(51) Int. Cl.
*A61B 5/00* (2006.01)
*G06Q 10/06* (2012.01)
*G16H 15/00* (2018.01)

(52) U.S. Cl.
CPC ...... *A61B 5/4806* (2013.01); *G06Q 10/06311* (2013.01); *G16H 15/00* (2018.01)

(58) Field of Classification Search
CPC . A61B 5/4806; G06Q 10/06311; G16H 15/00
See application file for complete search history.

(56) References Cited

U.S. PATENT DOCUMENTS

| | | |
|---|---|---|
| 5,433,223 A | 7/1995 | Moore-Ede |
| 7,118,530 B2 | 10/2006 | Hursh et al. |
| 7,898,426 B2 | 3/2011 | Rai |
| 2002/0005784 A1 | 1/2002 | Balkin et al. |
| 2003/0225856 A1 | 12/2003 | Pietrowski |
| 2005/0149852 A1 | 7/2005 | Bleicher |
| 2008/0215407 A1 | 9/2008 | Pachon |

(Continued)

FOREIGN PATENT DOCUMENTS

| | | |
|---|---|---|
| EP | 2278508 | 1/2011 |
| JP | 10-91691 | 4/1998 |
| JP | 2001/256598 | 9/2001 |
| JP | 2012/048310 | 3/2012 |
| WO | WO 2014066059 | 5/2014 |

OTHER PUBLICATIONS

Authorized Officer Athina Nickitas-Etienne, International Preliminary Report on Patentability for International Application No. PCT/US2015/045079, dated Mar. 2, 2017, 7 pages.

(Continued)

*Primary Examiner* — Eliza A Lam
(74) *Attorney, Agent, or Firm* — Fish & Richardson P.C.

(57) ABSTRACT

There is provided a research framework system. For example, in some implementations there is provided a sleep prediction system for pilots including a first data structure storing collected research data related to pilot sleep patterns, a second data structure storing data related to a flight schedule associated with a pilot, and a sleep prediction module configured to access the data stored in the first and second data structures and calculate, by one or more processors using the data stored in the first data structure, a likelihood that the pilot associated with the flight schedule stored in the second data structure is sleeping at a given time.

20 Claims, 9 Drawing Sheets

(56) References Cited

U.S. PATENT DOCUMENTS

| | | | |
|---|---|---|---|
| 2011/0071873 A1* | 3/2011 | Vaughan | G06Q 10/0635 |
| | | | 705/7.28 |
| 2012/0029971 A1* | 2/2012 | Lee | G06Q 10/06 |
| | | | 705/7.28 |
| 2012/0232414 A1 | 9/2012 | Mollicone et al. | |
| 2014/0187871 A1 | 7/2014 | Carrazo | |
| 2016/0048658 A1 | 2/2016 | Rangan | |

OTHER PUBLICATIONS

Authorized Officer Claude Berthon, International Search Report and Written Opinion for International Application No. PCT/US2015/045079, dated Oct. 13, 2015, 10 pages.

Biological Clocks and Shift Work Scheduling, Hearings before the subcommittee on Investigations and oversight of the committee on science and technology house of representatives, Mar. 23, 24, 1983 pp. 68-69 (Year: 1983).

Japanese Notice of Allowance in Japanese Application No. 2017/528756, dated Mar. 9, 2020.

Japanese Office Action in Japanese Application No. 2017/528756, dated Jul. 8, 2019, 5 pages.

Koji Miyamoto et al., "Healthcare technology for realizing a healthy and lively society—Wearable Sensors Corresponding to Various Applications in Healthcare Field", Toshiba Review, Japan, Toshiba corporation, Nov. 1, 2014, vol. 69, No. 11, 7 pages (publication showing well-known technology) [No English version available].

Signal et al., "Sleep Measurement in Flight Crew: Comparing Actigraphic and Subjective Estimates to Polysomnography" Aviat Space Environ Med. Nov. 2005; 76(11):1058-63.

* cited by examiner

270 ⬎

| PVT Profile Manager | 🗕🗖✕ |
|---|---|
| PVT Profile ID | 5 ▾ |
| Description | XYZ Smartphone |
| Manufacturer | ABC Manufacturer |
| Manufacturer Model | ABCD-123 |
| Manufacturer Device ID | A34567 |
| Size | 10x10 |
| Weight | 0.2lbs |
| Software | PVT Mobile |
| Operating System | Android |
| OS Version | 4.1.1 |
| Test Interface | Touch Screen |

| New Profile | ADD | UPDATE | DELETE | COPY |

| Crew Profile Manager | 🗕🗖✕ |
|---|---|
| Study Reference | 87D ▾ |
| Crew Profile ID | 1 ▾ |
| Crew Reference ID | 1001 ▾ |
| Gender | M ▾ |
| Age Group | 45-49 ▾ |
| Residing Time Zone | -5 ▾ |
| Landings | 0-99 ▾ |
| Flight Hours | 0-999 ▾ |
| Commute Type | Air Other ▾ |
| Commute Hrs | 3 ▾ |

| New Pro... | ADD | UPDATE | DELETE | COPY |

FIG. 5B

Subject Configuration Manager

Choose Panel

Study Profiles

- 16 | 2014 BidYear - IND AFW Consecutive Night Hub Turns.
- 8 | Domestic Multiple 24 Hour Layovers. Body Clock Swaps
- 1 | JULY BidMonth - All Domestic IND Hub Turns
- 6 | AUG BidMonth - ALL Domestic IND AFW Hub Turns. MEM base.
- 9 | Sept BidMonth - IND AFW Consecutive Night Hub Turns
- 10 | Europe 4 Consecutive Nights, CGN Domicile Pilots in Europe
- 11 | Europe, 4 Consecutive Nights, CGN Domicile North america Pilots
- 12 | International. Go Around the World. Eastward. No or Limited Deadheads
- 13 | International. Go Around the World. Westwards. Regular Line Pilots
- 14 | International. Go Around the World. Westwards. Management Only
- 15 | International. Go Around the World. Eastwards. Management Only

| Crew Profiles | Schedule Profiles | Actigraph Profiles | PVT Profiles |
|---|---|---|---|
| 1 \| 2050 | 84 \| 11 EUR57 2013-10-06 | 2 \| A03750 Phillips Respironics | 1 \| S1 Pulsar |
| 2 \| 2051 | 85 \| 20 EUR57 2013-10-06 | 26 \| A03891 Phillips Respironics | 3 \| S2 Pulsar |
| 3 \| 2052 | 86 \| 27 EUR57 2013-10-06 | 1 \| A03989 Phillips Respironics | 4 \| S3 Pulsar |
| 4 \| 2053 | 87 \| 3 EUR57 2013-10-06 | 25 \| A04011 Phillips Respironics | |
| 5 \| 2054 | 88 \| 7 EUR57 2013-10-06 | 24 \| A04200 Phillips Respironics | |
| 6 \| 2055 | 89 \| 1 EUR57 2013-10-07 | 3 \| A11519 Phillips Respironics | |
| 7 \| 2056 | 90 \| 20 EUR57 2013-10-13 | 17 \| A11549 Phillips Respironics | |
| 8 \| 2057 | 91 \| 7 EUR57 2013-10-13 | 18 \| A11556 Phillips Respironics | |
| 9 \| 2058 | 92 \| 1 EUR57 2013-10-14 | 16 \| A11557 Phillips Respironics | |
| 10 \| 2059 | 93 \| 11 EUR57 2013-10-20 | 10 \| A11673 Phillips Respironics | |
| 11 \| 2060 | 94 \| 20 EUR57 2013-10-20 | 19 \| A11679 Phillips Respironics | |
| 12 \| 2061 | 95 \| 27 EUR57 2013-10-20 | 8 \| A11682 Phillips Respironics | |
| 13 \| 2062 | 96 \| 3 EUR57 2013-10-20 | 5 \| A11684 Phillips Respironics | |
| 14 \| 2063 | 97 \| 7 EUR57 2013-10-20 | 6 \| A11686 Phillips Respironics | |

FIG. 6

| Configuration Panel | | | | | |
|---|---|---|---|---|---|
| ID# | Study# | Crew Profile# | Schedule# | Actigraph# | PVT# |
| 109 | 10 | 9 | 91 | 20 | 0 |
| 110 | 10 | 10 | 100 | 0 | 0 |
| 111 | 10 | 11 | 90 | 4 | 0 |
| 112 | 10 | 12 | 94 | 24 | 0 |
| 113 | 10 | 13 | 104 | 18 | 0 |
| 114 | 10 | 14 | 100 | 26 | 0 |
| 115 | 10 | 15 | 97 | 14 | 0 |
| 116 | 10 | 16 | 93 | 0 | 0 |
| 118 | 10 | 18 | 96 | 17 | 0 |
| 119 | 10 | 19 | 94 | 0 | 3 |
| 120 | 10 | 20 | 95 | 1 | 0 |
| 121 | 10 | 21 | 98 | 4 | 0 |
| 194 | 10 | 10 | 93 | 19 | 1 |

[ New Configure ] [ Update Configurations ] [ Delete Configure ]

FIG. 6 (Cont.)

RESEARCH PERFORMANCE FRAMEWORK

CROSS-REFERENCE TO RELATED APPLICATION

This application is a continuation of U.S. application Ser. No. 14/460,995, filed on Aug. 15, 2014. The entire disclosure of the above application is incorporated herein by reference.

BACKGROUND

This disclosure relates generally to electronic systems and more particularly to the systems for managing the performance of research studies, such as studies related to subjects sleep and performance measures. It is essential in many industries to conduct a wide array of clinical, medical, and/or behavioral studies. Conducting these studies requires the manual coordination between numerous study principals, takes months of data compilation and analysis prior to receiving any results, and usually does not permit study adjustments, interim results, or real-time analysis of study data.

SUMMARY

There is provided a research framework system including a physical condition measurement device configured to measure a physical condition of a study subject, a first networked device communicatively coupled to the physical condition measurement device and configured to receive one or more physical condition measurements related to the study subject from the physical condition measurement device, a second networked device communicatively coupled to the first networked device over a network, the second networked device configured to perform the following operations using one or more processors: receive the physical condition measurement from the first networked device; store the received physical condition measurement in a data structure with physical condition measurements from a plurality of other study subjects, and provide an interface to perform a study assessment using the physical condition measurement of the study subject and the plurality of other study subjects. A system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions.

The physical condition measurement device may be configured to automatically measure a physical condition an aircraft pilot. The second networked device may be configured to provide a prediction of a pilot attribute based at least partially on the physical condition measurements. The first networked device may include a smart phone that is communicative coupled to the physical condition measurement device via a wireless network.

There is also provided a sleep prediction system having a first data structure storing collected research data related to pilot sleep patterns; a second data structure storing data related to a flight schedule associated with a pilot; and a sleep prediction module configured to: access the data stored in the first and second data structures; and process, by one or more processors using the data stored in the first data structure, a likelihood that the pilot associated with the flight schedule stored in the second data structure is sleeping at a given time. Other embodiments of this aspect include corresponding computer systems, apparatus, and computer programs recorded on one or more computer storage devices, each configured to perform the actions of the methods.

The sleep prediction system may be implemented such that at least a portion of the data related to pilot sleep patterns was automatically collected via one or more physical condition measurement devices associated with one or more pilots and/or where at least a portion of the data related to pilot sleep patterns was collected by one or more subjective surveys of one or more pilots. The sleep prediction module may be configured to generate a graphical display of pilot sleep patterns based at least partially on the data stored in the first data structure. The sleep prediction system may also include one or more physical condition measurement devices coupled to one or more pilots, wherein the one or more physical condition measurement devices are configured to transmit data to the first data structure over a network.

There is also provided a process including providing a first networked communication device for use by a study participant, receiving, using one or more processors, a study instruction, wherein the study instruction instructs the study participant to alter one or more study conditions, automatically updating data stored in a research-related data structure based at least partially on the instruction to the study participant, and communicating the instruction to the first networked communication device over a network. Other implementations of this aspect may include corresponding computer systems, apparatus, and computer programs recorded on one or more computer storage devices, each configured to perform the process.

This process may include providing a second networked communication device for use by a study researcher, wherein the second networked communication device is configured to enable the study researcher to generate the study instruction. This process may also include providing third networked communication device for use by a study research assistant; and communicating the instruction to the third networked communication device over the network, wherein the study instruction further directs the study research assistant to alter a research study condition. This process may also include providing fourth networked communication device for use by a study sponsor, wherein the fourth networked communication device is configured to enable the study sponsor to monitor progress of the study. This process may also include automatically receiving study related measurement data from the first networked communication device and automatically storing the received measurement data in one or more data structure associated with a research study. This process may also include generating one or more graphical screens to display a statistical analysis of the received measurement data.

There is also provided a process including receiving over a network a first plurality of analytical data related to one or more study participants, wherein the first plurality of data includes data automatically collected by one or more physical condition measurement device worn by one or more study participants, receiving a second plurality of analytical data including data associated with one or more external conditions related to each of the one or more study participants, and automatically creating, using one or more processors, a visual representation of a statistical analysis of the first plurality of analytical data and the second plurality of analytical data. Other embodiments of this aspect include corresponding computer systems, apparatus, and computer programs recorded on one or more computer storage devices, each configured to perform the process. This method may also include receiving a third plurality of manually entered data, wherein the manually entered data comprises data recorded by the one or more study participants. This method may also include receiving the first plurality of analytical data comprises receiving data recorded by an actigraph. The method may also include receiving the second plurality of analytical data comprises receiving data recorded by a light sensor.

BRIEF DESCRIPTION OF THE DRAWINGS

FIG. 5A is an example profile generation screen for a PVT device in accordance with example implementations;

FIG. 5B is an example profile modification screen for a crew profile in accordance with example implementations;

FIG. 6 is an example screen that may be used to assign one or more profiles to a particular study subject;

DETAILED DESCRIPTION

In some implementations described below, a research performance framework may be designed to perform a variety of research enabling and research study analysis functions. For example, the research performance framework may be configured to conduct a research study into pilot sleep schedules via performance measurements and provide statistical results on the research topic and provide predictions of future sleep patterns for pilots that enable better flight operations planning.

Figure 1:
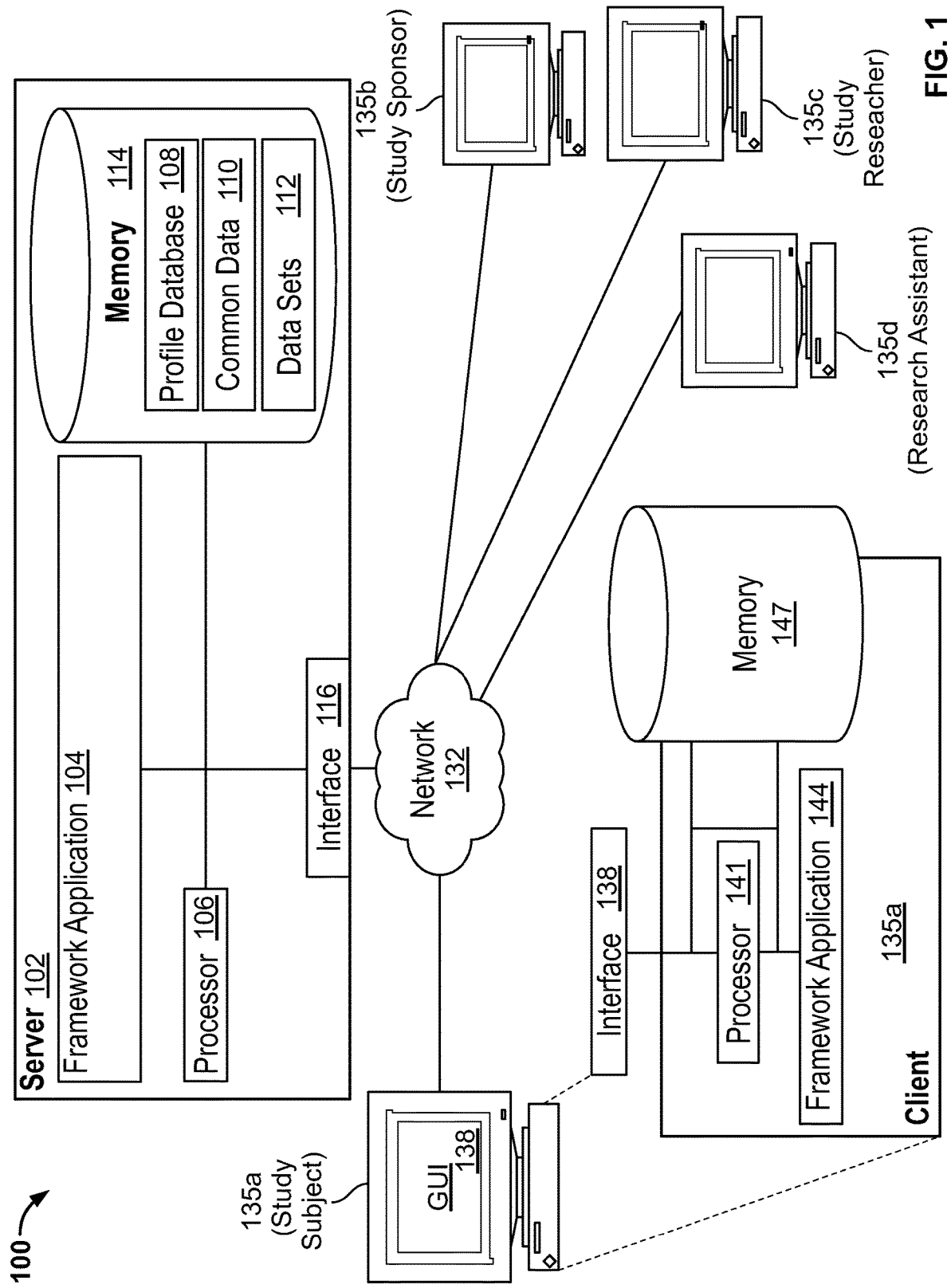
FIG. 1 is a block diagram of an example research framework system in accordance with example implementation.

Turning to the example implementation of FIG. 1, the illustrated system 100 includes or is communicably coupled with a server 102 and one or more clients 135, at least some of which communicate across network 132. In general, the system 100 depicts an example configuration of a system capable of providing a research performance framework via the server 102 and the clients 135.

In general, the server 102 is any server that stores one or more applications, such as the framework application 104. The framework application may be executed as software or hardware. In some instances, the server 102 may store a plurality of applications in addition to the framework application 104, while in other instances, the server 102 may be a dedicated server meant to store and execute only the framework application 104. In some instances, the server 102 may comprise a web server, where the framework application 104 is one or more web-based applications accessed and executed via network 132 by the clients 135 of the system to perform the programmed tasks or operations of the framework application 104.

At a high level, the server 102 comprises an electronic computing device operable to receive, transmit, process, store, or manage data and information associated with the system 100. As used in the present disclosure, the term "computer" or "computing device" is intended to encompass any suitable processing device. For example, although FIG. 1 illustrates a single server 102, system 100 can be implemented using two or more servers 102, as well as computers other than servers, including a server pool. Indeed, server 102 may be any computer or processing device such as, for example, a blade server, general-purpose personal computer (PC), Macintosh, workstation, UNIX-based workstation, or any other suitable device. In other words, the present disclosure contemplates computers other than general purpose computers, as well as computers without conventional operating systems. Further, illustrated server 102 may be adapted to execute any operating system, including Linux, UNIX, Windows, Mac OS, or any other suitable operating system. According to one embodiment, server 102 may also include or be communicably coupled with an air traffic control system or a flight management system.

In some implementations, and as shown in FIG. 1, the server 102 includes a processor 106, an interface 116, a memory 114, and framework application 104. The interface 116 is used by the server 102 for communicating with other systems in a client-server or other distributed environment (including within system 100) connected to the network 132 (e.g., client 135, as well as other systems communicably coupled to the network 132). Generally, the interface 116 comprises logic encoded in software and/or hardware in a suitable combination and operable to communicate with the network 132. More specifically, the interface 116 may comprise software supporting one or more communication protocols associated with communications such that the network 132 or interface's hardware is operable to communicate physical signals within and outside of the illustrated system 100.

Generally, the network 132 facilitates wireless or wireline communications between the components of the system 100 (i.e., between the server 102 and the clients 135), as well as with any other local or remote computer, such as additional clients, servers, or other devices communicably coupled to network 132 but not illustrated in FIG. 1. The network 132 is illustrated as a single network in FIG. 1, but may be a continuous or discontinuous network without departing from the scope of this disclosure, so long as at least a portion of the network 132 may facilitate communications between senders and recipients.

In still other examples, the network 132 may include a messaging backbone. The network 132 may be all or a portion of an enterprise or secured network, while in another instance at least a portion of the network 132 may represent a connection to the Internet. In some instances, a portion of the network 132 may be a virtual private network (VPN), such as, for example, the connection between the client 135 and the server 102. Further, all or a portion of the network 132 can comprise either a wireline or wireless link. Example wireless links may include 802.11a/b/g/n, 802.20, WiMax, and/or any other appropriate wireless link. In other words, the network 132 encompasses any internal or external network, networks, sub-network, or combination thereof operable to facilitate communications between various computing components inside and outside the illustrated system 100.

The network 132 may communicate, for example, Internet Protocol (IP) packets, Frame Relay frames, Asynchronous Transfer Mode (ATM) cells, voice, video, data, and other suitable information between network addresses. The network 132 may also include one or more local area networks (LANs), radio access networks (RANs), metropolitan area networks (MANs), wide area networks (WANs), all or a portion of the Internet, and/or any other communication system or systems at one or more locations.

As illustrated in FIG. 1, server 102 includes a processor 106. Although illustrated as a single processor 106 in FIG. 1, two or more processors may be used according to particular needs, desires, or particular embodiments of system 100. Each processor 106 may be a central processing unit (CPU), a blade, an application specific integrated circuit (ASIC), a field-programmable gate array (FPGA), or another suitable component. Generally, the processor 106 executes instructions and manipulates data to perform the operations of server 102 and, specifically, framework application 104. Specifically, the server's processor 106 executes the functionality required to receive and respond to requests from the clients 135 and their respective client framework applications 144, as well as the functionality required to perform the other operations of the framework application 104.

Regardless of the particular implementation, "software" may include computer-readable instructions, firmware, wired or programmed hardware, or any combination thereof on a tangible medium operable when executed to perform at least the processes and operations described herein. Indeed, each software component may be fully or partially written or described in any appropriate computer language including C, C++, Java, Visual Basic, assembler, Perl, any suitable version of 4GL, as well as others. It will be understood that while portions of the software illustrated in FIG. 1 are shown as individual modules that implement the various features and functionality through various objects, methods, or other processes, the software may instead include a number of sub-modules, third party services, components, libraries, and such, as appropriate. Conversely, the features and functionality of various components can be combined into single components as appropriate.

The framework application 104 may be implemented may be implemented as Enterprise Java Beans (EJBs) or design-time components and may have the ability to generate run-time implementations into different platforms, such as J2EE (Java 2 Platform, Enterprise Edition), ABAP (Advanced Business Application Programming) objects, or Microsoft's .NET, among others. Additionally, the framework application 104 may be a web based application accessed and executed by remote clients 135 or client framework applications 144 via the network 132 (e.g., through the Internet). Further, while illustrated as internal to server 102, one or more processes associated with a framework application 104 may be stored, referenced, or executed remotely. For example, a portion of the framework application 104 may be a web service associated with the application that is remotely called, while another portion framework application 104 may be an interface object or agent bundled for processing at a remote client 135. Still further, portions of the framework application 104 may be executed by a user working directly at server 102, as well as remotely at client 135.

The server 102 also includes memory 114. Memory 114 may include any memory or database module and may take the form of volatile or non-volatile memory including, without limitation, magnetic media, optical media, random access memory (RAM), read-only memory (ROM), removable media, or any other suitable local or remote memory component. Memory 114 may store various objects or data, including classes, frameworks, applications, backup data, business objects, jobs, web pages, web page templates, database tables, repositories storing business and/or dynamic information, and any other appropriate information including any parameters, variables, algorithms, instructions, rules, constraints, or references thereto associated with the purposes of the server 102 and the framework application 104. Additionally, memory 114 may include any other appropriate data, such as VPN applications, firmware logs and policies, firewall policies, a security or access log, print or other reporting files, as well as others.

At a high level, the memory 114 may include three data structures—a profile database 108, a common data structure 110, and a results data set structure 112, each of which are described below with regard to FIG. 2. It should be understood, however, that the structures 108, 110, and 112 are merely exemplary and in other implementations, the memory 114 and indeed any suitable data storage used by the framework application 104 may be organized in a variety of suitable organizations. In various implementations, the data structures 108, 110, and 112 may be stored as part of the framework application 104 or in another suitable storage location.

The system 100 may also include one or more clients 135. Each client 135 may be any computing device operable to connect to or communicate with at least the server 102 and/or via the network 132 using a wireline or wireless connection. Further, as illustrated by client 135a, each client 135 includes a processor 141, an interface 138, a graphical user interface (GUI) 138, a client application 144, and a memory 147. In general, each client 135 comprises an electronic computer device operable to receive, transmit, process, and store any appropriate data associated with the system 100 of FIG. 1. It will be understood that there may be any number of clients 135 associated with, or external to, system 100. For example, while illustrated system 100 includes four clients (135a, 135b, 135c, and 135d), alternative implementations of system 100 may include a single client 135 communicably coupled to the server 102, or any other number suitable to the purposes of the system 100.

Additionally, there may also be one or more additional clients 135 external to the illustrated portion of system 100 that are capable of interacting with the system 100 via the network 132. Further, the term "client" and "user" may be used interchangeably as appropriate without departing from the scope of this disclosure. Moreover, while each client 135 is described in terms of being used by a single user, this disclosure contemplates that many users may use one computer, or that one user may use multiple computers. As used in this disclosure, client 135 is intended to encompass a personal computer, touch screen terminal, workstation, network computer, kiosk, wireless data port, smart phone, personal data assistant (PDA), a dedicated research terminal, one or more processors within these or other devices, or any other suitable processing device.

The clients 135 may also be "smart" or internet enabled appliances. For example, the clients may be measurement devices or sensors capable of independent and automatic communication over one or more networks. The clients may be any suitable form measurement device or sensor including, but not limited to, activity meters, sleep sensors, actigraph devices, psychomotor vigilance task (PVT) devices, pedometer, body temperature sensors, medical sensors (such as heart rate sensors or blood pressure sensors), light sensors, telemetry sensors, and/or circadian sensors. For example, in some implementations, one of the clients 135 may include a physical sensor configured to communication over a wireless network either by itself or in combination with a smart phone, such as Bluetooth enabled sensor in communication with a smartphone or tablet computer.

Each client 135 may comprise a computer that includes an input device, such as a keypad, touch screen, mouse, or other device that can accept user information, and an output device that conveys information associated with the operation of the server 102 (and framework application 104) or the client 135 itself, including digital data, visual information, the client application 144, or the GUI 138. Both the input and output device may include fixed or removable storage media such as a magnetic or solid state storage media or other suitable media to both receive input from and provide output to users of the clients 135 through the display, namely, the GUI 138. As described above, in many implementations, one or more of the clients may be a networked device or computer system.

As indicated in FIG. 1, the clients 135 may be associated with particular users of the system 100. For example, the client 135a may be associated with a study subject, such as a pilot. Client 135b may be associated with a study sponsor, such as a corporation or governmental interest that may fund the performance of a research study. Client 135c may be associated with a study researcher, such as a research scientist, that formulates a research study and tracks its progress. Client 135d may be associated with a research assistant that is responsible for interacting with the study subjects during the course of the study. It will be understood, however, that the assignment of clients 135 in FIG. 1 is exemplary and clients 135 may be assigned or associated with study principals in any suitable manner. One of the clients or the server 102 may communicate one or more study condition or instructions over the network 132 to another one of the clients 135, such as study subject or study research assistant. In this way, the system 100 may enable a study principal, such as a study scientist or study sponsor, to communicate study conditions and instructions to automatically and/or efficiently to study principals in one or more studies via a single study framework. It will also be understood that the system 100 may include a variety of additional clients 135 not illustrated in FIG. 1, such as administrator or network support systems.

Further, the illustrated clients 135 include a GUI 138 comprising a graphical user interface operable to interface with at least a portion of system 100 for any suitable purpose, including generating a visual representation of the client application 144 (in some instances, the client's web browser) and the interactions with the framework application 104, including the responses received from the framework application 104 received in response to the requests sent by the client application 144. Generally, through the GUI 138, the user is provided with an efficient and user-friendly presentation of data provided by or communicated within the system. The term "graphical user interface," or GUI, may be used in the singular or the plural to describe one or more graphical user interfaces and each of the displays of a particular graphical user interface. Therefore, the GUI 138 can represent any graphical user interface, including but not limited to, a web browser, touch screen, or command line interface (CLI) that processes information in system 100 and efficiently presents the information results to the user.

In general, the GUI 138 may include a plurality of user interface (UI) elements, some or all associated with the client application 144, such as interactive fields, pull-down lists, and buttons operable by the user at client 135. These and other UI elements may be related to or represent the functions of the client application 144, as well as other software applications executing at the client 135. In particular, the GUI 138 may be used to present the client-based perspective of the framework application 104, and may be used (as a web browser or using the client application 144 as a web browser) to view and navigate the framework application 104, as well as various web pages located both internal and external to the server, some of which may be associated with the framework application 104.

For purposes of the present location, the GUI 138 may be a part of or the entirety of the client application 144, while also merely a tool for displaying the visual representation of the client and framework application 104 actions and interactions. In some instances, the GUI 138 and the client application 144 may be used interchangeably, particularly when the client application 144 represents a web browser associated with the framework application 104.

While FIG. 1 is described as containing or being associated with a plurality of elements, not all elements illustrated within system 100 of FIG. 1 may be utilized in each alternative implementation of the present disclosure. Additionally, one or more of the elements described herein may be located external to system 100, while in other instances, certain elements may be included within or as a portion of one or more of the other described elements, as well as other elements not described in the illustrated implementation. Further, certain elements illustrated in FIG. 1 may be combined with other components, as well as used for alternative or additional purposes in addition to those purposes described herein.

Figure 2:
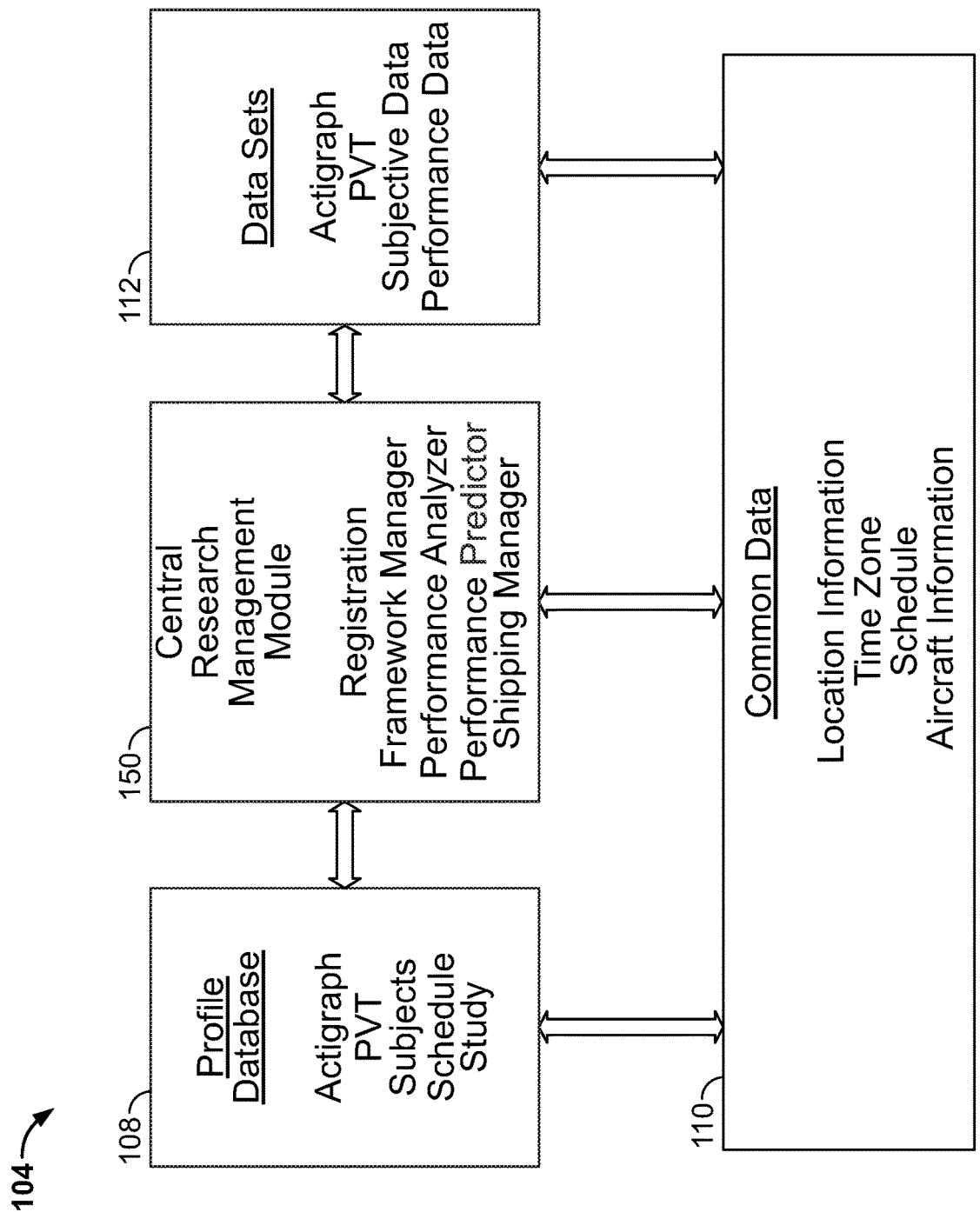
FIG. 2 is a flow chart of an example process for changing application state in accordance with example implementations.

Turning next to FIG. 2, a block diagram of an example implementation of the framework application 104 in communication with data structures 108, 110, and 112 is shown. The framework 104 may include a central research management module 150. As shown in FIG. 2, the module 150 is configured to communicate with the structures 108, 110, and 112 to create and manage research studies. For example, the module 150 may be configured to provide a registration capability, such as to add a new study to the system 100 or to add a new study principal, such as a study subject or research assistant. As described below in regard to FIG. 4, the framework application 104 may perform registration by adding one or more profiles to the profile database 108.

Next, the module 150 may include a framework manager that enables management of one or more research studies by the system 100 and communication between study principals, over the network 132 (for example) using one or more processors in the server 102 and the clients 135. The framework manager may also enable a study principal, such as a study researcher or a study sponsor, to configure one or more parameters of the study, including but not limited to the number of participants, the length of the study, or the goals of the study. The framework manager may also be configured, as described below, to permit the entry or adjust of a variety of study profiles, including subject profiles, device profiles, and schedule profiles.

The module 150 may also include a performance analyzer that is configured to analyze, calculate, and/or assess the results of research study. If the framework application 104 is being used in a study involving sleep, such as a study directed to pilot sleep, the module 150 may also include a sleep analyzer. As described below, the performance analyzer may be configured to receive study result data either manually or automatically from one or more physical condition measurement devices. For example, the performance analyzer can be configured to determine sleep/wake interruptions, to determine opportunities for sleep, or to determine sleep patterns. In some implementations, the performance analyzer may be a part of the framework manager.

The module 150 may also include a performance predictor. The performance predictor can be configured to process data, such as data from the data sets 112 and predict a future value of a study variable and/or condition. For example, in the case of pilot study, the performance predictor may be configured to analyze sleep data for one or more pilots based on one or more references or profiles, such as time, aircraft, route, timezone, etc., and to generate predictive data regarding the likely sleep for a pilot associated with that reference or profile.

The performance predictor enables the framework application 104 to be used predictively to evaluate the effects of changes to the profile to the study results. For example, a study researcher can via one or more processors to adjust a study profiles or assessment to generate predictive data from the system 100 regarding the future predicted performance of one or more study subjects. This predictive data could then be used either automatically or manually to assign one or more pilots, routes, schedules, or flight plans. In some implementations, the framework application 104 may use an iterative process to evaluate predictive outcomes for varying conditions for study subjects or similar populations. For example, the framework application may iteratively perform a fatigue prediction for pilots and predict those pilots based on the study results that are likely to have the least or lower fatigue when flying a particular route, schedule aircraft, etc. However, this is only an example and the framework application 104 may be used to predict performance of based on any suitable study characteristic.

The module 150 may also include one or more administrative managers or functions. For example, FIG. 2 illustrates that module 150 include a shipping manager that is configured to manage the shipping of study materials to study principals, such as the subjects or the research assistants.

As shown in FIG. 2, the profile database 108 is a data structure configured to store one or more research study profiles. A profile is a general configuration structure that defines one or more variables associated with a physical device, a study participant, or other study aspect. For example, as shown in FIG. 2, the profile database 108 may include one or more physical device profiles, such as actigraph profiles, for example, Actiwatch 2 or Actiwatch Spectrum, PVT device profiles, sleep monitor profiles, and so forth. The profile database may also include subject profiles. The profile database 108 may also include schedule profiles that define one or more research or flight schedule. The profile database 108 may further include one or more other study related profiles. Notably, as described further below, the profiles in the profile database 108 may be created and modified by one the study principals using the research framework 104.

The framework application 104 may also be coupled to a common data structure 110 in some implementations. The common data structure 110 may include a database of environmental and external conditions or factors that change less often than the profile data and generally affect the research study. In the example shown in FIG. 2, the common data 110 includes location information, schedule information, time zone, and aircraft information, for example. The common data 110 may also include landing information, sleep types, regions, commute length information, country information, measurement scales, and/or a wide variety of other study related data depending on the type of study being managed by the framework application 104.

Next, the framework application may be coupled to one or more data sets 112. The data sets 112 include the data collected by the study. In some implementations, the collection of the data in the data sets 112 may be performed automatically by the client 135a. For example, the client 135a may be configured to use a physical condition measurement device, such as an actigraph or PVT device, to automatically record one or more physical condition measurements using one or more processors and on a periodic basis automatically upload study data to the framework 104 over the network 132.

The data sets 112 may also be populated using anyone of number of other suitable techniques. For example, the data in the data sets may be manually entered either by a study subject, such as by a pilot, or by a research assistant. A pilot could manually enter information on the client 135 from a sleep schedule or a fatigue log, and the client would then upload that information to the data sets 112. The data sets 112 may also be populated via one or more tests or trials performed by the research assistant. For example, the research assistant may administer a reaction test to a pilot and record the results (via the client 135d) to the data sets 112.

Figure 3:
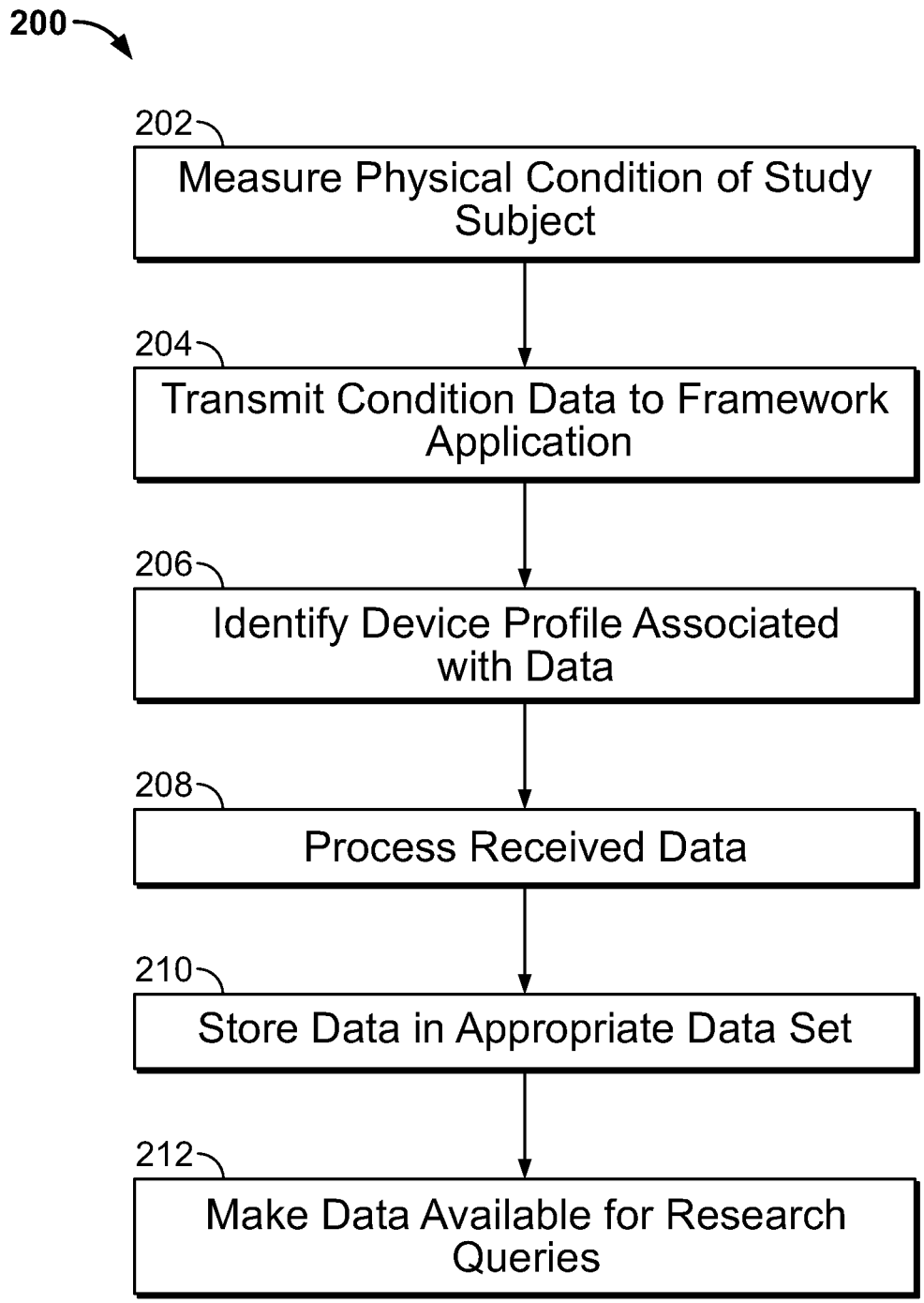
FIG. 3 is a flow chart of an example mobile device display screen in accordance with example implementations.

FIG. 3 is a flow chart of example process 200 for automatically collecting and compiling physical study data from study subjects. In some implementations, the process 200 may be performed by the framework application 104 and/or the client 135a. As shown in FIG. 3, the process 200 may begin by measuring a physical condition of a study subject, as shown in block 202. In some implementations, the physical condition measurement may be performed automatically by one or more physical condition measurement devices configured to communicate with or be a part of the client 135a, such as by a physical condition measurement device coupled via Bluetooth with a smartphone or tablet. As described above, the physical condition of the study subject may be measure by any suitable clinical, medical, or environmental sensor or measurement device. For example, the measurement may be taken by an actigraph device, PVT device, sleep sensor, temperature sensor, activity sensor, or darkness sensor. In some implementations, the device taking the measurement may not be physical connected to the study subject, for example, the sensor taking the measurement may located in the subject's environment or elsewhere.

As shown in block 204, the next step in the process 200 may involve the transmission via one or more processors and the network 132 of the physical condition measurement data to the framework application 104. For example, the client 135a may transmit data collected from an actigraph device over the internet to the server 102 upon which the framework application 104 is executing.

As shown in block 206, the next step in the process 200 may include identifying a device profile associated with the physical condition measurement data provided. For example, the framework application 104 may identify that the physical condition measurement data was collected by a particular model of actigraph device. Next, the framework application 104 may process the received data in view of the profile of the measurement device to extract desired study data, as shown in block 208. In some examples, the framework application may process the received data to compiled sleep schedule or an activity schedule.

Next, as shown in block 210, the process 200 may include storing the data in a data set associated with the processed physical data. For example, the processed data may be stored in one more data sets 112. Lastly, the process 200 may include making the data available for research queries, as shown in block 212. For example, the framework application 104 may enable the querying of the data set and the real time production of one or more graphically displays of research data to enable the selection of pilots or the assignment of pilot schedules.

Figure 4:
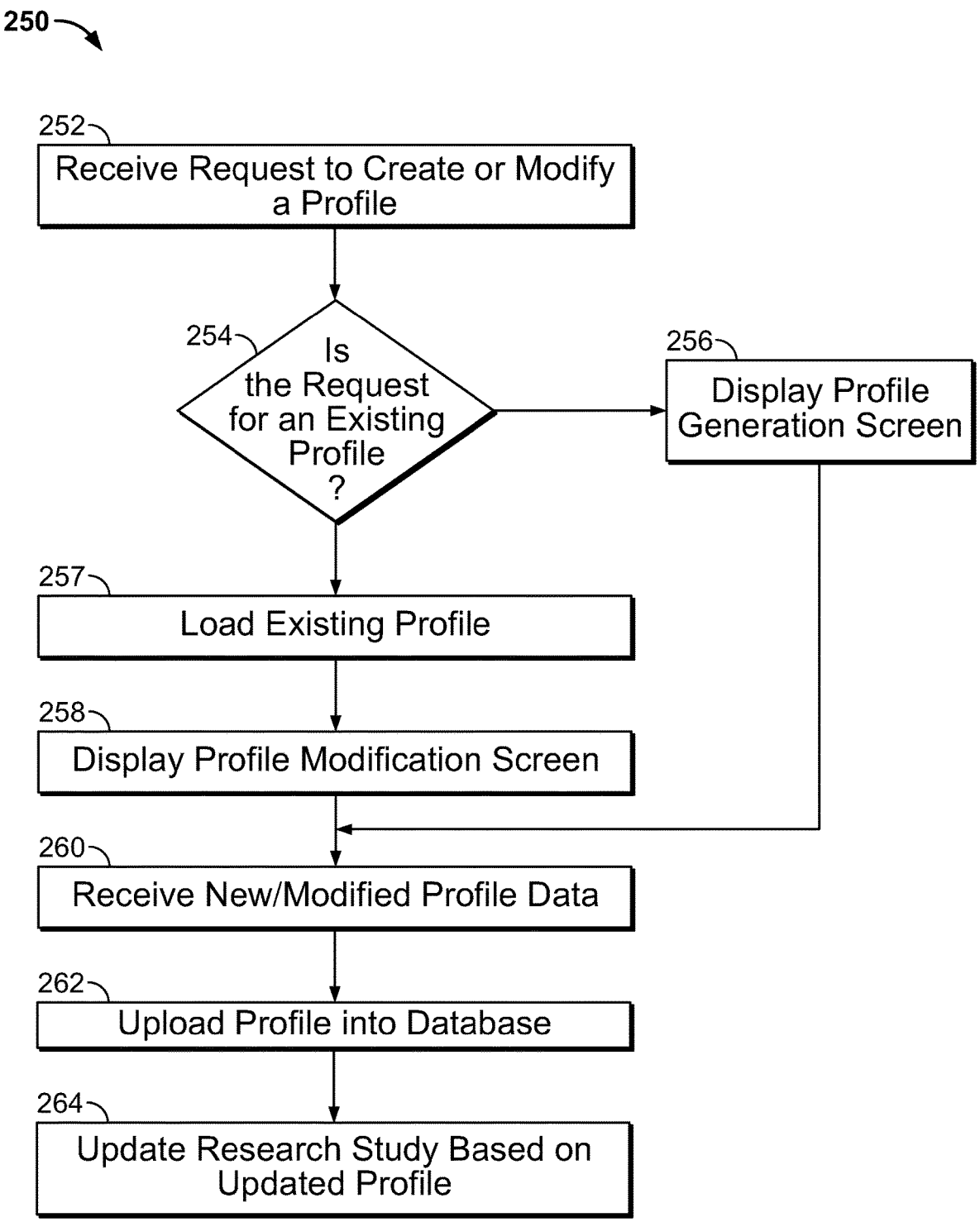
FIG. 4 is a flow chart of another example process for changing application state in accordance with example implementations.

FIG. 4 is a flow chart of an example process 250 for creating or modifying a study profile. The process 250 may be used by the framework application 104 to enable a study principal to add or modify a subject profile, device profile, or other suitable study profile. As shown in FIG. 4, the process 250 may begin with a request from a study principal to create or modify a profile, such as a physical device profile or a study profile. For example, in some implementations, the request may be a request to create a profile for an actigraph device that will be worn by a study subject.

As shown in FIG. 4, the process 250 may continue with block 254 with determining whether the request is associated with an existing profile. If the request is not associated with an existing profile, a screen to generate a new profile may be created, as shown in block 256. If on the other hand, there is an existing profile associated with the request, that profile will be loaded, as shown in block 257, and a profile modification screen will be displayed on GUI 138, as shown by block 258.

Exemplary profile generation/management screens are shown in FIGS. 5A and 5B. As illustrated, an example profile generation screen for a PVT device 270 is shown in FIG. 5A. As shown, the profile generation screen includes one or more data entry fields that enable a study principal to enter relevant information related to a particular profile. In the case of the illustrated PVT device, the profile could include a profile ID, a description, a manufacturer, a model number, a size, a weight, and software name and version numbers among other information. As noted above, the use of individual profiles for devices, studies, crews, and subjects enables both simpler design and management of the study and the study equipment, but also the ability to the modify conditions, participants, or equipment of the study with relatively little disruption to the study, the subjects, or the research assistants.

FIG. 5B illustrates an example profile modification screen 280 for a crew profile. As illustrated, the screen 280 may include a variety of data fields related to an aircraft crew-member that may be involved in a study. The framework application 104 may be configured to populate the fields in the screen 280 with information from the profile database 108 to enable a study principal to modify one or more attributes of the crew profile.

Returning to FIG. 4, next, the process 250 may include receiving new or modified profile data from a study principal, as shown in block 260. The profile data can then be uploaded into the profile database 108, as shown in block 262. Lastly, as shown in block 264, once a profile is updated in the profile database, the framework application 104 may update research study information based on the updated profile. The framework application will also be configured to apply the updated profile to newly received research data received from the client 135a. In this way, the framework application 104 is enables a study principal, such as a study researcher or research assistant, to replace or change study devices or participants throughout the progress of study without the need to abandon an existing study and begin anew.

Once profiles are created or modified, configurations may be created for the one or more study subjects. FIG. 6 shows an example screen 300 that may be used to assign study subject configurations. The screen 300 may be displayed on the GUI 138 or on another display in the system 100. The screen 300 provides an interface for a study principal to assign one or more study configurations to a particular study subject. For example, FIG. 6 depicts the assignment of a study profile number, crew profile number, schedule profile number, actigraph device profile number and PVT device profile number to a plurality of study subjects identified by ID number. Advantageously, the screen 300 via one or more processors 106 on the server 102 enables a study principal to dynamically adjust the profiles associates with a particular study subject based on study changes, such as a change in equipment or a change in flight schedule.

Figure 7:
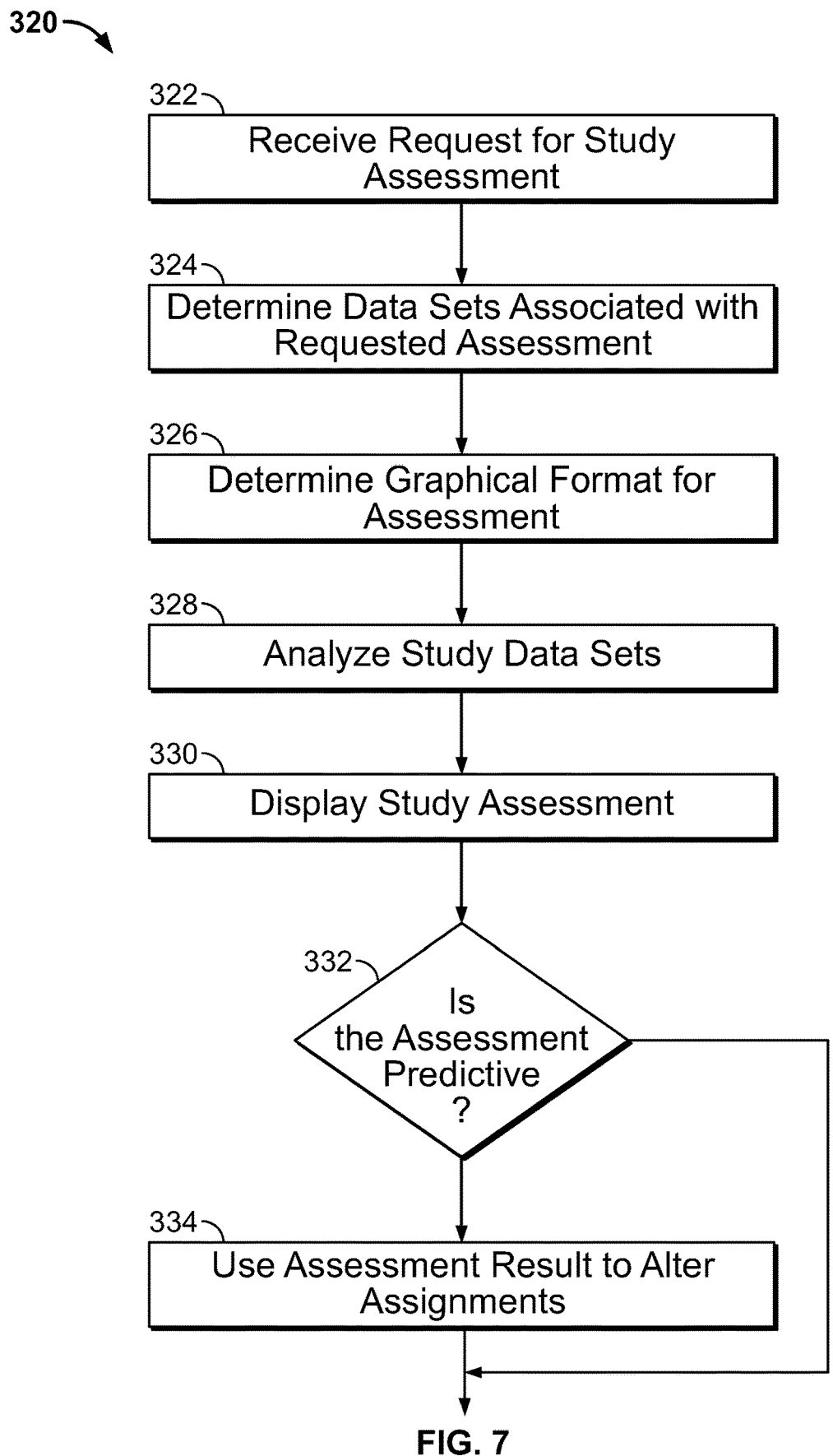
FIG. 7 is a flow chart of an example process for assessing the results of a research study.

Turning next to FIG. 7, a flow chart of an example process 320 for assessing the results of a research study is shown. In some implementation, the process 320 may be performed by the application framework 104 or another suitable component in the system 100. As an example, the process 320 is described in the context of a pilot sleep assessment, but it should be understood that the process 320 might be used to assess the results of a variety of suitable forms of research studies.

As shown by block 322, the process 320 may begin by receiving a request for a study assessment. In various examples, a study assessment may involve analyzing and displaying the results of an on-going study—including real time results collected from the clients 135a-d—and/or may involve calculating a predictive analysis (as described above), for example, a prediction of future pilot performance based on flight time.

The process 320 continues as shown in block 324 by determining what data sets, such as the data sets 108, are needed to perform the requested study assessment. In various implementations, determining the data sets involves identify one or more flight data related data set that were automatically collected from pilots. In various implementations, determining the data sets may also include identifying data from the profile database 108, the common data 110, or other suitable storage locations.

Next, the process 320 involves determining a graphical format for assessment, as shown in block 326. The format for the assessment may be determined by the framework application 104 based on preset selections, may be dynamically assigned based on a characteristic of the study, and/or may be selected based on a user choice. The graphical format will be used to display the results of the study assessment, although in some implementations, the assessment may be displayed non-graphically, for example as summary text results.

The process 320 then involves performing an analysis of the data sets, such as a statistical analysis of the data sets 112, to produce the study assessment, as shown by block 328. In various embodiments, the analysis of the study data sets may include determining sleep wake curves, determining performance at various hours of the day or into a flight, determining the interplay between any collected study data, or any other desired analysis of the study data. The statistical analysis may involve analyzing the data on the basis of sleep times, time of day, initial condition or fatigue, schedule, geographic location, time zone, and/or other suitable factors. In some implementations, the study assessment may include performing a dynamic intersections between two or more data sets to identify commonalities, probabilities, or other statistical relationships between the data stored in the data sets 112.

Next, the study assessment may be displayed, as shown by block 332. In some implementations, the study assessment may be displayed on the GUI 138, although any suitable display device may also be used. Lastly, the process 320 may determine if the requested study assessment was a predictive assessment, such as a predictive assessment of performance, as indicated by block 332. If the assessment was predictive, the process 320 may next involve changing a study related assignment in view of the assessment. For example, the process 320 may involve changing a flight schedule or a crew assignment based on a predictive assessment of pilot performance or of pilot sleep/wake patterns. In some implementations, the process 320 may involve providing a pilot assignment recommendation based on the study assessment result. For example, the framework application may be configured to statistical calculate a pilot with a high percentage chance of being sufficiently rested based on data stored within the data sets. In some implementations the process 320 may include merging the results of multiple studies and/or comparing subjects or group of subjects across those multiple studies.

Figure 8:
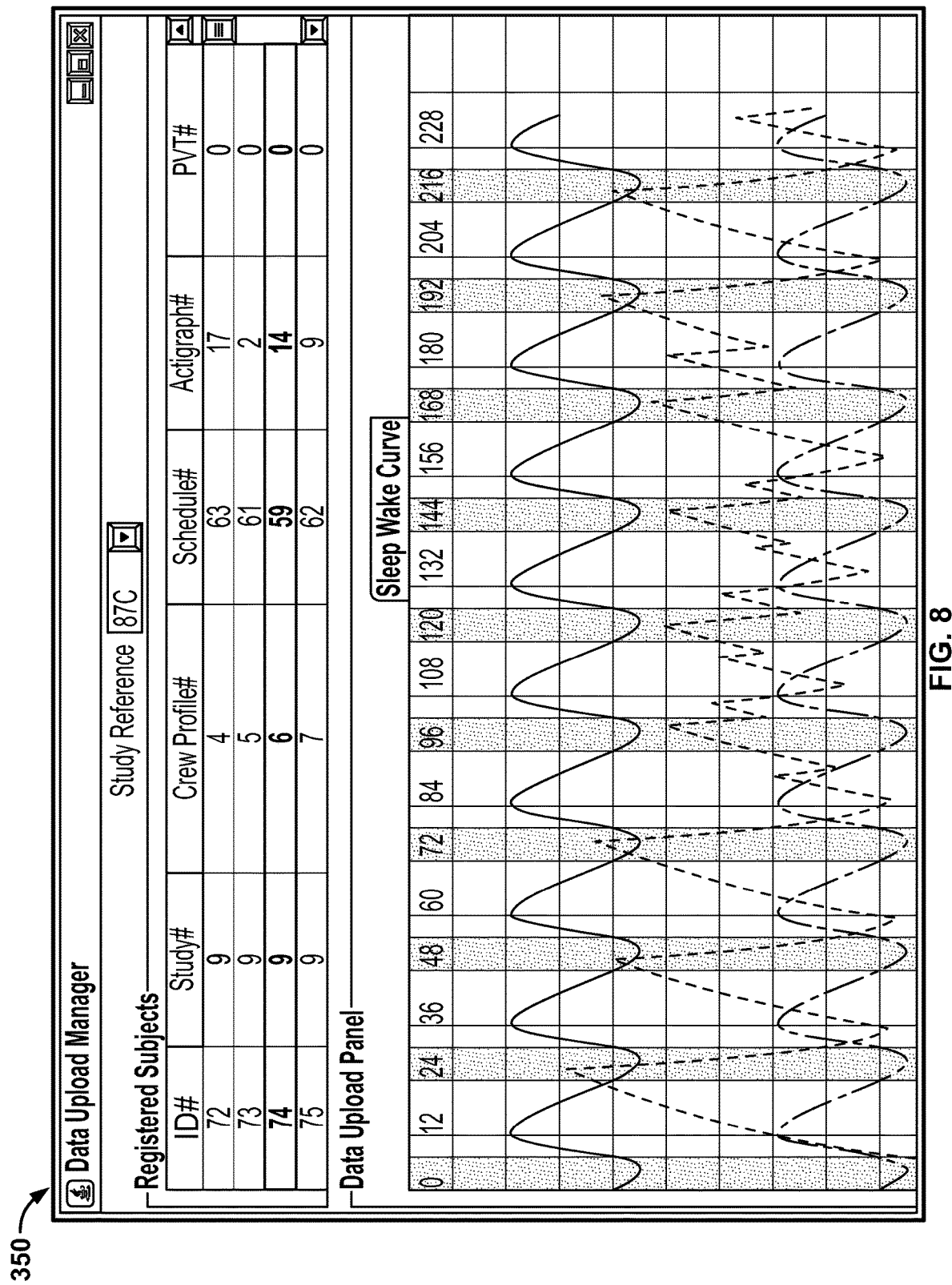
FIG. 8 is an example screen that may be used to display study assessment results for a particular study subject.

FIG. 8 shows an example screen 350 that may be used to display study assessment results for a particular study subject. In particular, the example screen 350 displays sleep pressure curves being generated in real-time or near realtime from one or more clients 135. As described above in relation to FIG. 7, the screen 350 and the assessment within it can be generated from the data set 108, including real time study data collected over the network 132. The study assessment on the screen 350 may be used either automatically by the system 100 or manually by a study principal to assign flight crews or aircraft routes. As noted above, however, the screen 350 is merely exemplary and in various implementations any suitable form of statistical or prediction analysis of the study data may be displayed on the screen 350 or other screens generated by the system 100.

While this document contains many specific implementation details, these should not be construed as limitations on the scope of what may be claimed, but rather as descriptions of features that may be specific to particular implementations or embodiments. Certain features that are described in this specification in the context of separate embodiments can also be implemented in combination in a single embodiment. Conversely, various features that are described in the context of a single embodiment can also be implemented in multiple embodiments separately or in any suitable sub combination. Moreover, although features may be described above as acting in certain combinations and even initially claimed as such, one or more features from a claimed combination can, in some cases, be excised from the combination, and the claimed combination may be directed to a sub combination or variation of a sub combination.

The invention claimed is:

1. A method executed by at least one processor of a flight management system, the method comprising:
    receiving over a network analytical data related to one or more study participants, wherein the analytical data includes data automatically collected by one or more actigraph sensors worn by one or more aircraft pilots;
    receiving one or more reference profiles including data associated with one or more pilot profiles related to each of the one or more aircraft pilots, wherein each pilot profile includes pilot experience data comprising a cumulative number of flight hours and a cumulative number of landings of a corresponding pilot;
    determining, by the flight management system and for each pilot, a predicted pilot performance by conducting iterative fatigue analysis on the analytical data and data contained in the one or more reference profiles; and
    automatically assigning one or more of the aircraft pilots to a flight in a flight schedule based on results of the predicted pilot performance.

2. The method of claim 1, wherein the one or more aircraft pilots are assigned to flights in the flight schedule based on which of the aircraft pilots are likely to have a lower fatigue when flying particular flights.

3. The method of claim 1, wherein receiving the analytical data comprises receiving data recorded by a light sensor.

4. The method of claim 1, wherein the one or more reference profiles include profiles that include scheduled flight times, flight crew sleep times, aircraft types, flight routes, geographic locations of flight crew members, or time zone profiles.

5. The method of claim 1 further comprising:
    identifying, based on the analytical data, a device profile associated with the actigraph sensor, the device profile indicating a particular model of the actigraph sensor; and
    processing the analytical data from the actigraph sensor in accordance with the device profile.

6. The method of claim 1 further comprising:
    responsive to a request to modify a selected reference profile from among the one or more reference profiles, providing, for display to a user, a profile modification interface that includes a plurality of user selectable options for modifying data contained in the selected reference profile;
    receiving, through the profile modification interface, user input indicating a modification to the selected reference profile;
    modifying the selected reference profile in accordance with the user input to provide a modified reference profile; and
    automatically re-determining the predicted pilot performance by conducting iterative fatigue analysis on the analytical data and data in the modified reference profile.

7. The method of claim 1 further comprising
    providing, for display to a user, a study configuration interface that includes a first list of a first set of user selectable reference profiles and a second list of a second set of user selectable reference profiles;
    receiving, through the study configuration interface, user input identifying a first particular reference profile form the first list and a second particular reference profile from the second list; and
    responsive to the user input, associating the first particular reference profile and the second particular reference profile with a study,
    wherein the predicted pilot performance is determined based on the first particular reference profile and the second particular reference profile.

8. A flight management system comprising:
    at least one processor; and a data store coupled to the at least one processor having instructions stored thereon which, when executed by the at least one processor, causes the at least one processor to perform operations comprising:
    receiving over a network analytical data related to one or more study participants, wherein the analytical data includes data automatically collected by one or more actigraph sensors worn by one or more aircraft pilots;
    receiving one or more reference profiles including data associated with one or more pilot profiles related to each of the one or more aircraft pilots, wherein each pilot profile includes pilot experience data comprising a cumulative number of flight hours and a cumulative number of landings of a corresponding pilot;

determining, for each pilot, a predicted pilot performance by conducting iterative fatigue analysis on the analytical data and data contained in the one or more reference profiles; and automatically assigning one or more of the aircraft pilots to a flight in a flight schedule based on results of the predicted pilot performance.

9. The system of claim 8, wherein the one or more aircraft pilots are assigned to flights in the flight schedule based on which of the aircraft pilots are likely to have a lower fatigue when flying particular flights.

10. The system of claim 8, wherein receiving the analytical data comprises receiving data recorded by a light sensor.

11. The system of claim 8, wherein the one or more reference profiles include profiles that include scheduled flight times, flight crew sleep times, aircraft types, flight routes, geographic locations of flight crew members, or time zone profiles.

12. The system of claim 8, wherein the operations further comprise:

identifying, based on the analytical data, a device profile associated with the actigraph sensor, the device profile indicating a particular model of the actigraph sensor; and processing the analytical data from the actigraph sensor in accordance with the device profile.

13. The system of claim 8, wherein the operations further comprise:

responsive to a request to modify a selected reference profile from among the one or more reference profiles, providing, for display to a user, a profile modification interface that includes a plurality of user selectable options for modifying data contained in the selected reference profile;

receiving, through the profile modification interface, user input indicating a modification to the selected reference profile;

modifying the selected reference profile in accordance with the user input to provide a modified reference profile; and automatically re-determining the predicted pilot performance by conducting iterative fatigue analysis on the analytical data and data in the modified reference profile.

14. The system of claim 8, wherein the operations further comprise:

providing, for display to a user, a study configuration interface that includes a first list of a first set of user selectable reference profiles and a second list of a second set of user selectable reference profiles;

receiving, through the study configuration interface, user input identifying a first particular reference profile form the first list and a second particular reference profile from the second list; and responsive to the user input, associating the first particular reference profile and the second particular reference profile with a study, wherein the predicted pilot performance is determined based on the first particular reference profile and the second particular reference profile.

15. A non-transitory computer readable storage medium storing instructions that, when executed by at least one processor, cause the at least one processor to perform operations comprising:

at least one processor; and a data store coupled to the at least one processor having instructions stored thereon which, when executed by the at least one processor, causes the at least one processor to perform operations comprising:

receiving over a network analytical data related to one or more study participants, wherein the analytical data includes data automatically collected by one or more actigraph sensors worn by one or more aircraft pilots;

receiving one or more reference profiles including data associated with one or more pilot profiles related to each of the one or more aircraft pilots, wherein each pilot profile includes pilot experience data comprising a cumulative number of flight hours and a cumulative number of landings of a corresponding pilot;

determining, for each pilot, a predicted pilot performance by conducting iterative fatigue analysis on the analytical data and data contained in the one or more reference profiles; and automatically assigning one or more of the aircraft pilots to a flight in a flight schedule based on results of the predicted pilot performance.

16. The medium of claim 15, wherein the one or more reference profiles include profiles that include scheduled flight times, flight crew sleep times, aircraft types, flight routes, geographic locations of flight crew members, or time zone profiles.

17. The medium of claim 15, wherein the operations further comprise:

identifying, based on the analytical data, a device profile associated with the actigraph sensor, the device profile indicating a particular model of the actigraph sensor; and processing the analytical data from the actigraph sensor in accordance with the device profile.

18. The medium of claim 15, wherein the operations further comprise:

responsive to a request to modify a selected reference profile from among the one or more reference profiles, providing, for display to a user, a profile modification interface that includes a plurality of user selectable options for modifying data contained in the selected reference profile;

receiving, through the profile modification interface, user input indicating a modification to the selected reference profile;

modifying the selected reference profile in accordance with the user input to provide a modified reference profile; and automatically re-determining the predicted pilot performance by conducting iterative fatigue analysis on the analytical data and data in the modified reference profile.

19. The medium of claim 15, wherein the operations further comprise:

providing, for display to a user, a study configuration interface that includes a first list of a first set of user selectable reference profiles and a second list of a second set of user selectable reference profiles;

receiving, through the study configuration interface, user input identifying a first particular reference profile form the first list and a second particular reference profile from the second list; and responsive to the user input, associating the first particular reference profile and the second particular reference profile with a study, wherein the predicted pilot performance is determined based on the first particular reference profile and the second particular reference profile.

20. The medium of claim 15, wherein receiving the analytical data comprises receiving data recorded by a light sensor.

* * * * *